(12) United States Patent  (10) Patent No.: US 8,425,560 B2
Massoudi  (45) Date of Patent: Apr. 23, 2013

(54) SPINAL IMPLANT DEVICE WITH FIXATION PLATES AND LAG SCREWS AND METHOD OF IMPLANTING

(76) Inventor: Farzad Massoudi, Corona Del Mar, CA (US)

( * ) Notice: Subject to any disclaimer, the term of this patent is extended or adjusted under 35 U.S.C. 154(b) by 62 days.

(21) Appl. No.: 13/043,821

(22) Filed: Mar. 9, 2011

(65) Prior Publication Data

US 2012/0232592 A1   Sep. 13, 2012

(51) Int. Cl.
*A61B 17/70* (2006.01)
(52) U.S. Cl.
USPC .......................................................... 606/249
(58) Field of Classification Search .................. 606/248, 606/249
See application file for complete search history.

(56) References Cited

U.S. PATENT DOCUMENTS

| | | | |
|---|---|---|---|
| 5,011,484 A * | 4/1991 | Breard | 606/249 |
| 5,558,674 A * | 9/1996 | Heggeness et al. | 606/278 |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,090,112 A | 7/2000 | Zucherman et al. | |
| 6,149,652 A | 11/2000 | Zucherman et al. | |
| 6,152,926 A | 11/2000 | Zucherman et al. | |
| 6,156,038 A | 12/2000 | Zucherman et al. | |
| 6,183,471 B1 | 2/2001 | Zucherman et al. | |
| 6,190,387 B1 | 2/2001 | Zucherman et al. | |
| 6,235,030 B1 | 5/2001 | Zucherman et al. | |
| 6,238,397 B1 | 5/2001 | Zucherman et al. | |
| 6,280,444 B1 | 8/2001 | Zucherman et al. | |
| 6,312,431 B1 | 11/2001 | Asfora | |
| 6,332,882 B1 | 12/2001 | Zucherman et al. | |
| 6,332,883 B1 | 12/2001 | Zucherman et al. | |
| 6,379,355 B1 | 4/2002 | Zucherman et al. | |
| 6,419,676 B1 | 7/2002 | Zucherman et al. | |
| 6,419,677 B2 | 7/2002 | Zucherman et al. | |
| 6,440,169 B1 | 8/2002 | Elberg et al. | |
| 6,451,019 B1 | 9/2002 | Zucherman et al. | |
| 6,451,020 B1 | 9/2002 | Zucherman et al. | |

(Continued)

FOREIGN PATENT DOCUMENTS

| | | |
|---|---|---|
| WO | WO2010019783 | 2/2010 |
| WO | WO2011019756 | 2/2011 |

OTHER PUBLICATIONS

Copenheaver, Blaine R., PCT International Search Report, Jul. 2, 2012, pp. 1-6.
Copenheaver, Blaine R., PCT International Search Report, Jun. 28, 2012, pp. 1-8.

*Primary Examiner* — Jerry Cumberledge
(74) *Attorney, Agent, or Firm* — Stetina Brunda Garred & Brucker (57) ABSTRACT

There is provided a spinal implant device for placement between adjacent spinous processes. The spinal implant device includes first and second fixation plates, a connector, and first and second lag screws. The first fixation plate includes a first and second screw holes. The second fixation plate includes third and fourth screw holes. The first lag screw extends through the first and third screw holes and threadedly engages a respective one of the first or third screw holes with the superior spinous process disposed between the first and second superior ends. The second lag screw extends through the second and fourth screw holes and threadedly engages a respective one of the second or fourth screw holes with the inferior spinous process disposed between the first and second inferior ends. A method of implanting the device is provided.

16 Claims, 5 Drawing Sheets

U.S. PATENT DOCUMENTS

| | | |
|---|---|---|
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,582,433 B2 | 6/2003 | Yun |
| 6,626,944 B1 | 9/2003 | Taylor |
| 6,652,527 B2 | 11/2003 | Zucherman et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,733,534 B2 | 5/2004 | Sherman |
| 6,761,720 B1 | 7/2004 | Senegas |
| 6,796,983 B1 | 9/2004 | Zucherman et al. |
| 6,902,566 B2 | 6/2005 | Zucherman et al. |
| 6,946,000 B2 | 9/2005 | Senegas et al. |
| 7,029,473 B2 | 4/2006 | Zucherman et al. |
| 7,087,083 B2 | 8/2006 | Pasquet et al. |
| 7,101,375 B2 | 9/2006 | Zucherman et al. |
| 7,163,558 B2 | 1/2007 | Senegas et al. |
| 7,189,234 B2 | 3/2007 | Zucherman et al. |
| 7,201,751 B2 | 4/2007 | Zucherman et al. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 8,048,120 B1 * | 11/2011 | Fallin et al. .................. 606/249 |
| 2002/0091446 A1 | 7/2002 | Zucherman et al. |
| 2002/0143331 A1 | 10/2002 | Zucherman et al. |
| 2003/0040746 A1 * | 2/2003 | Mitchell et al. ................ 606/61 |
| 2003/0153915 A1 | 8/2003 | Nekozuka et al. |
| 2003/0220643 A1 | 11/2003 | Ferree |
| 2004/0097931 A1 | 5/2004 | Mitchell |
| 2004/0153071 A1 | 8/2004 | Zucherman et al. |
| 2004/0167520 A1 | 8/2004 | Zucherman et al. |
| 2004/0193159 A1 | 9/2004 | Zucherman et al. |
| 2004/0220568 A1 | 11/2004 | Zucherman et al. |
| 2004/0249379 A1 * | 12/2004 | Winslow et al. ................ 606/61 |
| 2005/0010293 A1 | 1/2005 | Zucherman et al. |
| 2005/0010298 A1 | 1/2005 | Zucherman et al. |
| 2005/0075634 A1 | 4/2005 | Zucherman et al. |
| 2005/0101955 A1 | 5/2005 | Zucherman et al. |
| 2005/0143738 A1 | 6/2005 | Zucherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0209603 A1 | 9/2005 | Zucherman et al. |
| 2005/0228383 A1 | 10/2005 | Zucherman et al. |
| 2005/0228384 A1 | 10/2005 | Zucherman et al. |
| 2005/0240182 A1 | 10/2005 | Zucherman et al. |
| 2005/0245929 A1 | 11/2005 | Winslow et al. |
| 2005/0245937 A1 | 11/2005 | Winslow |
| 2005/0261768 A1 | 11/2005 | Trieu |
| 2005/0288672 A1 | 12/2005 | Ferree |
| 2006/0004447 A1 | 1/2006 | Mastrorio |
| 2006/0015181 A1 | 1/2006 | Elberg |
| 2006/0036258 A1 | 2/2006 | Zucherman et al. |
| 2006/0036259 A1 | 2/2006 | Carl et al. |
| 2006/0064165 A1 | 3/2006 | Zucherman et al. |
| 2006/0064166 A1 | 3/2006 | Zucherman et al. |
| 2006/0084983 A1 | 4/2006 | Kim |
| 2006/0084985 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0089654 A1 | 4/2006 | Lins et al. |
| 2006/0089718 A1 | 4/2006 | Zucherman et al. |
| 2006/0106381 A1 | 5/2006 | Ferree et al. |
| 2006/0106397 A1 | 5/2006 | Lins |
| 2006/0122620 A1 | 6/2006 | Kim |
| 2006/0136060 A1 | 6/2006 | Taylor |
| 2006/0149383 A1 | 7/2006 | Arnin et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0235521 A1 | 10/2006 | Zucherman et al. |
| 2006/0241601 A1 | 10/2006 | Trautwein et al. |
| 2006/0241610 A1 | 10/2006 | Lim et al. |
| 2006/0247623 A1 | 11/2006 | Anderson et al. |
| 2006/0247634 A1 | 11/2006 | Warner et al. |
| 2006/0247640 A1 | 11/2006 | Blackwell et al. |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271049 A1 | 11/2006 | Zucherman et al. |
| 2006/0271055 A1 | 11/2006 | Thramann |
| 2006/0271194 A1 | 11/2006 | Zucherman et al. |
| 2006/0293662 A1 | 12/2006 | Boyer et al. |
| 2007/0005064 A1 | 1/2007 | Anderson et al. |
| 2007/0010813 A1 | 1/2007 | Zucherman et al. |
| 2007/0016303 A1 | 1/2007 | Jackson |
| 2007/0032790 A1 | 2/2007 | Aschmann et al. |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0049934 A1 | 3/2007 | Edidin et al. |
| 2007/0049935 A1 | 3/2007 | Edidin et al. |
| 2007/0055237 A1 | 3/2007 | Edidin et al. |
| 2007/0055246 A1 | 3/2007 | Zucherman et al. |
| 2007/0073292 A1 | 3/2007 | Kohm et al. |
| 2007/0093823 A1 | 4/2007 | Booth et al. |
| 2007/0093825 A1 | 4/2007 | Ferree et al. |
| 2007/0093828 A1 | 4/2007 | Abdou |
| 2007/0093830 A1 | 4/2007 | Zucherman et al. |
| 2007/0100340 A1 | 5/2007 | Lange et al. |
| 2007/0106298 A1 | 5/2007 | Carli et al. |
| 2007/0112354 A1 | 5/2007 | Iwasaki et al. |
| 2007/0123861 A1 | 5/2007 | Dewey et al. |
| 2007/0149972 A1 | 6/2007 | Nakajima et al. |
| 2007/0161992 A1 | 7/2007 | Kwak et al. |
| 2007/0161993 A1 | 7/2007 | Lowery et al. |
| 2007/0162000 A1 | 7/2007 | Perkins |
| 2007/0162005 A1 | 7/2007 | Peterson et al. |
| 2007/0167945 A1 | 7/2007 | Lange et al. |
| 2007/0173818 A1 | 7/2007 | Hestad et al. |
| 2007/0173821 A1 | 7/2007 | Trieu |
| 2007/0173823 A1 | 7/2007 | Dewey et al. |
| 2007/0173832 A1 | 7/2007 | Tebbe et al. |
| 2007/0185490 A1 | 8/2007 | Implicito |
| 2007/0191837 A1 | 8/2007 | Trieu |
| 2007/0191838 A1 | 8/2007 | Bruneau et al. |
| 2007/0191847 A1 | 8/2007 | Arnin et al. |
| 2007/0191947 A1 | 8/2007 | Arnin et al. |
| 2007/0191948 A1 | 8/2007 | Arnin et al. |
| 2007/0191949 A1 | 8/2007 | Arnin et al. |
| 2007/0191950 A1 | 8/2007 | Arnin et al. |
| 2007/0203490 A1 | 8/2007 | Zucherman et al. |
| 2007/0203491 A1 | 8/2007 | Pasquet et al. |
| 2007/0203493 A1 | 8/2007 | Zucherman et al. |
| 2007/0203494 A1 | 8/2007 | Arnin et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208347 A1 | 9/2007 | Zucherman et al. |
| 2007/0213724 A1 | 9/2007 | Arnin et al. |
| 2007/0213824 A1 * | 9/2007 | Trieu ......................... 623/17.11 |
| 2007/0213829 A1 | 9/2007 | Le Couedic et al. |
| 2007/0219552 A1 | 9/2007 | Zucherman et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233083 A1 | 10/2007 | Abdou |
| 2007/0233088 A1 | 10/2007 | Edmond |
| 2007/0233096 A1 | 10/2007 | Garcia-Bengochea |
| 2007/0233098 A1 | 10/2007 | Mastrorio et al. |
| 2007/0233118 A1 | 10/2007 | McLain |
| 2007/0233129 A1 | 10/2007 | Bertagnoli et al. |

| | | |
|---|---|---|
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0270823 A1 | 11/2007 | Trieu et al. |
| 2007/0270825 A1 | 11/2007 | Carls et al. |
| 2007/0270826 A1 | 11/2007 | Trieu et al. |
| 2007/0270829 A1 | 11/2007 | Carls et al. |
| 2007/0270834 A1 | 11/2007 | Bruneau et al. |
| 2007/0270840 A1* | 11/2007 | Chin et al. .................... 606/61 |
| 2007/0272259 A1 | 11/2007 | Allard et al. |
| 2007/0276368 A1 | 11/2007 | Trieu et al. |
| 2007/0276370 A1 | 11/2007 | Altarac et al. |
| 2007/0276372 A1 | 11/2007 | Malandain et al. |
| 2007/0276373 A1 | 11/2007 | Malandain |
| 2007/0276381 A1 | 11/2007 | Butler et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2007/0282340 A1 | 12/2007 | Malandain |
| 2007/0282442 A1 | 12/2007 | Malandain et al. |
| 2007/0282443 A1 | 12/2007 | Globerman et al. |
| 2007/0288006 A1 | 12/2007 | Arnin et al. |
| 2007/0299526 A1 | 12/2007 | Malandain |
| 2008/0004706 A1 | 1/2008 | Arnin et al. |
| 2008/0009866 A1 | 1/2008 | Alamin et al. |
| 2008/0009947 A1 | 1/2008 | Arnin et al. |
| 2008/0009948 A1 | 1/2008 | Arnin et al. |
| 2008/0015609 A1 | 1/2008 | Trautwein et al. |
| 2008/0015693 A1 | 1/2008 | Le Couedic |
| 2008/0015700 A1 | 1/2008 | Zucherman et al. |
| 2008/0021460 A1 | 1/2008 | Bruneau et al. |
| 2008/0021468 A1 | 1/2008 | Zucherman et al. |
| 2008/0021471 A1 | 1/2008 | Winslow et al. |
| 2008/0021472 A1 | 1/2008 | Winslow et al. |
| 2008/0021560 A1 | 1/2008 | Zucherman et al. |
| 2008/0021561 A1 | 1/2008 | Zucherman et al. |
| 2008/0027433 A1 | 1/2008 | Kohm et al. |
| 2008/0027434 A1 | 1/2008 | Zucherman et al. |
| 2008/0027435 A1 | 1/2008 | Zucherman et al. |
| 2008/0027438 A1 | 1/2008 | Abdou |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033552 A1 | 2/2008 | Lee et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0033560 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039944 A1 | 2/2008 | Malandain et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0046089 A1 | 2/2008 | Zucherman et al. |
| 2008/0051785 A1 | 2/2008 | Zucherman et al. |
| 2008/0051891 A1 | 2/2008 | Malandain et al. |
| 2008/0051892 A1 | 2/2008 | Malandain et al. |
| 2008/0051893 A1 | 2/2008 | Malandain et al. |
| 2008/0051894 A1 | 2/2008 | Malandain et al. |
| 2008/0051895 A1 | 2/2008 | Malandain et al. |
| 2008/0051896 A1 | 2/2008 | Suddaby |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0051906 A1 | 2/2008 | Malandain et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058934 A1 | 3/2008 | Malandain et al. |
| 2008/0058935 A1 | 3/2008 | Malandain et al. |
| 2008/0058936 A1 | 3/2008 | Malandain et al. |
| 2008/0058937 A1 | 3/2008 | Malandain et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071376 A1 | 3/2008 | Kohm et al. |
| 2008/0071378 A1 | 3/2008 | Zucherman et al. |
| 2008/0071380 A1 | 3/2008 | Sweeney |
| 2008/0082118 A1 | 4/2008 | Edidin et al. |
| 2008/0082167 A1 | 4/2008 | Edidin et al. |
| 2008/0082172 A1 | 4/2008 | Jackson et al. |
| 2008/0086212 A1 | 4/2008 | Zucherman et al. |
| 2008/0108990 A1 | 5/2008 | Mitchell et al. |
| 2008/0114358 A1 | 5/2008 | Anderson et al. |
| 2008/0114455 A1 | 5/2008 | Lange et al. |
| 2008/0114456 A1 | 5/2008 | Dewey et al. |
| 2008/0132952 A1 | 6/2008 | Malandain et al. |
| 2008/0147190 A1 | 6/2008 | Dewey et al. |
| 2008/0147192 A1 | 6/2008 | Edidin et al. |
| 2008/0161818 A1 | 7/2008 | Kloss et al. |
| 2008/0161822 A1 | 7/2008 | Perez-Cruet |
| 2008/0167655 A1 | 7/2008 | Wang et al. |
| 2008/0167656 A1 | 7/2008 | Zucherman et al. |
| 2008/0167657 A1 | 7/2008 | Greenhalgh |
| 2008/0172057 A1 | 7/2008 | Zucherman et al. |
| 2008/0177264 A1 | 7/2008 | Alamin et al. |
| 2008/0177271 A1 | 7/2008 | Yeh |
| 2008/0177272 A1 | 7/2008 | Zucherman et al. |
| 2008/0177298 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0177391 A1 | 7/2008 | Mitchell et al. |
| 2008/0183210 A1 | 7/2008 | Zucherman et al. |
| 2008/0183211 A1* | 7/2008 | Lamborne et al. ............ 606/249 |
| 2008/0183218 A1 | 7/2008 | Mueller et al. |
| 2008/0195152 A1 | 8/2008 | Altarac et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234735 A1* | 9/2008 | Joshi ............................ 606/247 |
| 2008/0234824 A1 | 9/2008 | Youssef et al. |
| 2008/0243250 A1 | 10/2008 | Seifert et al. |
| 2008/0249528 A1 | 10/2008 | Khalife |
| 2008/0255616 A1 | 10/2008 | Atkinson et al. |
| 2008/0255668 A1 | 10/2008 | Fallin et al. |
| 2008/0255669 A1 | 10/2008 | Fallin et al. |
| 2008/0262549 A1 | 10/2008 | Bennett et al. |
| 2008/0262617 A1 | 10/2008 | Froehlich et al. |
| 2008/0262619 A1 | 10/2008 | Ray |
| 2008/0281360 A1 | 11/2008 | Vittur et al. |
| 2008/0281361 A1 | 11/2008 | Vittur et al. |
| 2008/0281423 A1 | 11/2008 | Sheffer et al. |
| 2008/0287997 A1 | 11/2008 | Altarac et al. |
| 2008/0288072 A1 | 11/2008 | Kohm |
| 2008/0288075 A1 | 11/2008 | Zucherman et al. |
| 2008/0288078 A1 | 11/2008 | Kohm et al. |
| 2008/0294199 A1 | 11/2008 | Kohm et al. |
| 2008/0294200 A1 | 11/2008 | Kohm et al. |
| 2008/0294263 A1 | 11/2008 | Altarac et al. |
| 2008/0300686 A1 | 12/2008 | Khoo |
| 2008/0300687 A1 | 12/2008 | Lin et al. |
| 2008/0312741 A1 | 12/2008 | Lee et al. |
| 2008/0319487 A1 | 12/2008 | Fielding et al. |
| 2008/0319549 A1 | 12/2008 | Greenhalgh et al. |
| 2008/0319550 A1 | 12/2008 | Altarac et al. |
| 2009/0005819 A1 | 1/2009 | Ben-Mokhtar et al. |
| 2009/0005873 A1 | 1/2009 | Slivka et al. |
| 2009/0012528 A1 | 1/2009 | Aschmann et al. |
| 2009/0018658 A1 | 1/2009 | Garcia |

| | | | | | |
|---|---|---|---|---|---|
| 2009/0018662 A1 | 1/2009 | Pasquet et al. | 2009/0062915 A1 | 3/2009 | Kohm et al. |
| 2009/0030523 A1 | 1/2009 | Taylor | 2009/0264927 A1 * | 10/2009 | Ginsberg et al. .............. 606/246 |
| 2009/0036925 A1 | 2/2009 | Sala et al. | 2010/0191287 A1 | 7/2010 | Bucci |
| 2009/0043342 A1 | 2/2009 | Freedland | 2011/0022090 A1 | 1/2011 | Gordon et al. |
| 2009/0054931 A1 | 2/2009 | Metz-Stavenhagen | | | |
| 2009/0054988 A1 | 2/2009 | Hess | | | |

* cited by examiner

SPINAL IMPLANT DEVICE WITH FIXATION PLATES AND LAG SCREWS AND METHOD OF IMPLANTING

CROSS-REFERENCE TO RELATED APPLICATIONS

The present patent application is related to U.S. patent Ser. No. 13/033,450 filed on Feb. 23, 2011, entitled SPINAL IMPLANT DEVICE WITH FUSION CAGE AND FIXATION PLATES AND METHOD OF IMPLANTING.

STATEMENT RE: FEDERALLY SPONSORED RESEARCH/DEVELOPMENT

Not Applicable

BACKGROUND

1. Technical Field

The present disclosure relates generally to spinal implant devices. More particularly, the present disclosure relates to spinal implant devices with fixation plates and lag screws, and methods of implanting the same.

2. Related Art

There have been a myriad of spinal implant devices and techniques for treating spinal conditions that focus on fusion of the various levels of the spine. Moreover, a myriad of fixation devices and techniques have been implemented. Such fixation techniques range from use of peticle or facet screws with attached connecting rods to interspinous devices interacting with the spinous processes (such as spacers attaching the spinous processes with screw or bands). Spinous process fixation is a minimally invasive method of stabilizing fusion constructs posteriorly across one or multiple motion segments which replaces the traditional more invasive and potentially dangerous pedicle screws. Spinous process fixation, since its emergence, has been biomechanically weakened and hampered by the method of spinous process fixation which has consisted of various spiny teeth engaging with and affixing to the bone. Further, many devices require specialized surgical tools. Many attempts have been made to improve upon these devices and procedures to be minimally invasive, require a minimum number of procedures, and reduce recovery time. Such attempts have been met with varying degrees of success.

In view of the foregoing, there is a need in the art for an improved spinal implant device and method of implanting the same.

BRIEF SUMMARY

In accordance with one embodiment, a spinal implant device is provided for placement between adjacent spinous processes. The spinous processes include a superior spinous process and an inferior spinous process. The spinal implant device includes first and second fixation plates, a connector, and first and second lag screws. The first fixation plate includes a first superior end and a first inferior end. The first superior end includes a first screw hole, first inferior end including a second screw hole, the first fixation plate being sized and configured to extend between and along the spinous processes with the first screw hole adjacent the superior spinous process and the second screw hole adjacent the inferior spinous process. The second fixation plate includes a second superior end and a second inferior end. The second superior end includes a third screw hole. The second inferior end includes a fourth screw hole. The second fixation plate is sized and configured to extend between and along the spinous processes with the third screw hole adjacent the superior spinous process and the fourth screw hole adjacent the inferior spinous process. The connector is connected to the first fixation plate between the first superior end and the first inferior end and to the second fixation plate between the second superior end and the second inferior end. The first lag screw is sized and configured to extend through the first and third screw holes and threadedly engage a respective one of the first or third screw holes with the superior spinous process disposed between the first and second superior ends. The second lag screw is sized and configured to extend through the second and fourth screw holes and threadedly engage a respective one of the second or fourth screw holes with the inferior spinous process disposed between the first and second inferior ends.

In accordance with various embodiments, the third screw hole may be threaded, and the first lag screw may be sized and configured to extend through the first screw hole and threadedly engage the third screw hole with the superior spinous process disposed between the first and second superior ends. In addition, the second screw hole may be threaded, and the second lag screw may be sized and configured to extend through the fourth screw hole and threadedly engage the second screw hole with the inferior spinous process disposed between the first and second inferior ends. The first fixation plate may be generally planar and defines a superficial/deep plane. The first screw hole may extend through the first fixation plate at an angle less than 90 degrees, such as in a range of 60 to 30 degrees, with respect to the superficial/deep plane. The first and second fixation plates may each be generally planar and define a superficial/deep plane. The first and second fixation plates may be configured to translate relative to each other along a lateral axis orthogonal to the superficial/deep planes. The first and second fixation plates may be angularly in fixed relation to each other. The connector may be a pin. The connector may be in the slidable engagement with the second fixation plate. The connector may have a non-circular cross-section. The connector may be in fixed relation to the first fixation plate. The first and second fixation plates may each include teeth for respectively engaging the spinous processes.

According to another embodiment, there is provided a method of implanting a spinal implant device for placement between adjacent spinous processes. The spinous processes include a superior spinous process and an inferior spinous process. The method includes providing the spinal implant device including first and second fixation plates. The first fixation plate includes a first superior end and a first inferior end. The first superior end includes a first screw hole. The first inferior end includes a second screw hole. The second fixation plate includes a second superior end and a second inferior end. The second superior end includes a third screw hole. The second inferior end includes a fourth screw hole.

According to various embodiments, the method further includes positioning the first fixation plate along the spinous processes with the first superior end adjacent the superior spinous process and the first inferior end adjacent the inferior spinous process. The method further includes positioning the second fixation plate along the spinous processes with the second superior end adjacent the superior spinous process and the second inferior end adjacent the inferior spinous process. The method further includes inserting a first lag screw through the first and third screw holes and superior spinous process. The method further includes threadedly engaging the first lag screw with a respective one of the first or third screw holes. The method further includes inserting a second lag screw through the second and fourth screw holes and inferior spinous process. The method further includes threadedly engaging the second lag screw with a respective one of the second or fourth screw holes. The first fixation plate may be generally planar and defining a superficial/deep plane. The first screw hole extends through the first fixation plate at an angle less than 90 degrees, such as in a range of 60 to 30 degrees with respect to the superficial/deep plane, with respect to the superficial/deep plane. The first and second fixation plates may include teeth, and the method may include positioning the teeth respectively against the spinous processes. The method may include drilling a hole through the superior spinous process. The method may further include providing a drill guide engaged with the first fixation plate, and inserting a drill bit through the drill guide through the first fixation plate and into the superior spinous process.

The present invention will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

The detailed description set forth below in connection with the appended drawings is intended as a description of certain embodiments of the present disclosure, and is not intended to represent the only forms that may be developed or utilized. The description sets forth the various functions in connection with the illustrated embodiments, but it is to be understood, however, that the same or equivalent functions may be accomplished by different embodiments that are also intended to be encompassed within the scope of the present disclosure. It is further understood that the use of relational terms such as top and bottom, first and second, and the like are used solely to distinguish one entity from another without necessarily requiring or implying any actual such relationship or order between such entities.

Figure 1:
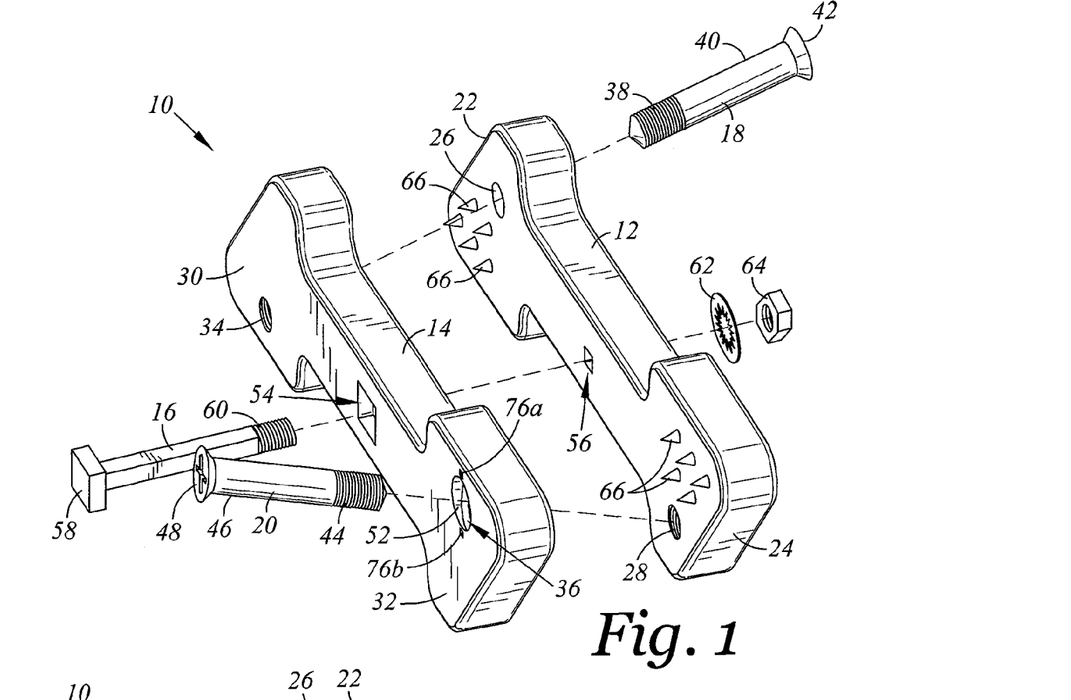
FIG. 1 is an exploded perspective view of a spinal implant device according to an embodiment of the invention.
Figure 2:
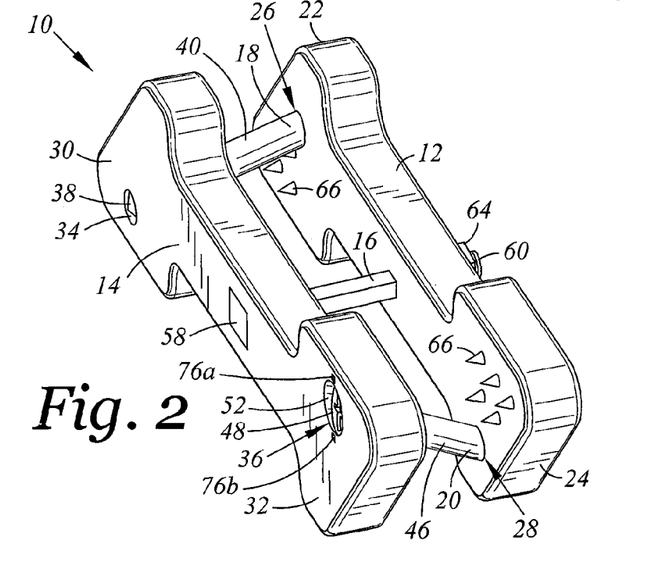
FIG. 2 is the spinal implant device of FIG. 1 as assembled.
Figure 3:
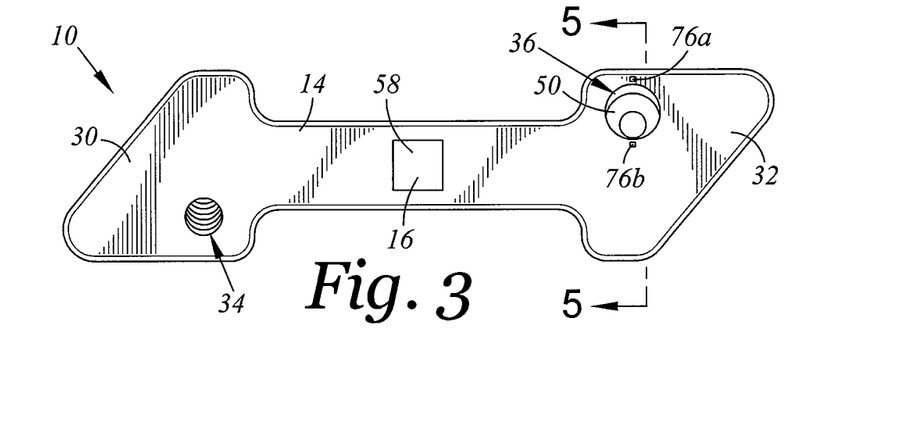
FIG. 3 is a side view of the spinal implant device of FIG. 2 (without any lag screws)
Figure 4:
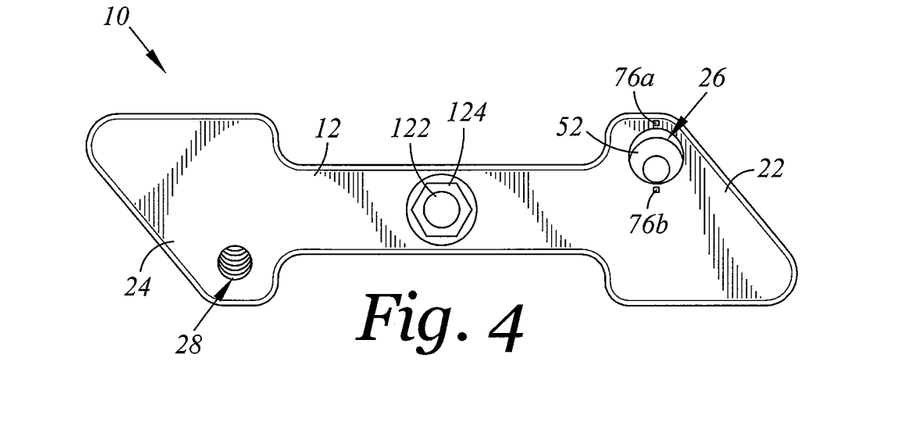
FIG. 4 is a reverse side view of the spinal implant device of FIG. 2 (without any lag screws)
Figure 5:
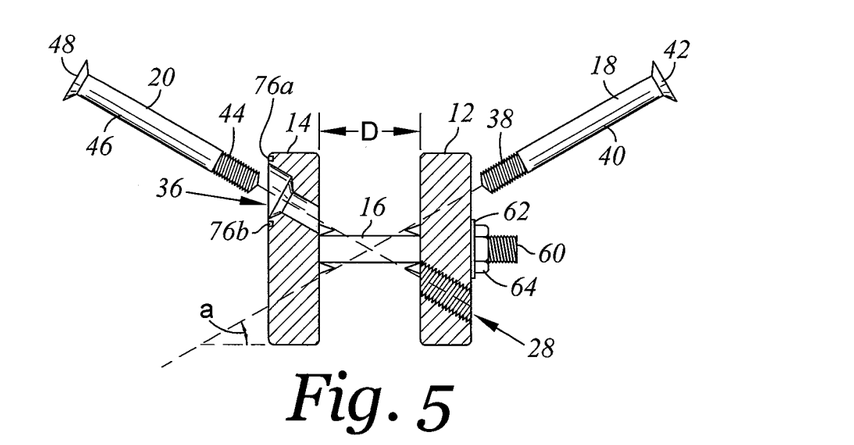
FIG. 5 is an end view of the spinal implant device of FIG. 2 with lag screws (exploded) as seen along axis 5-5.

Referring now to FIG. 1, there is depicted an exploded perspective view of a spinal implant device 10 according to an embodiment of the invention. FIG. 2 is the spinal implant device 10 of FIG. 1 as assembled. FIG. 3 is a side view of the spinal implant device 10 of FIG. 2 (without any lag screws), and FIG. 4 is a reverse side of the spinal implant device 10 of FIG. 2 (without any lag screws). FIG. 5 is an end view of the spinal implant device 10 of FIG. 2 with lag screws 18, 20 (exploded) as seen along axis 5-5.

Figure 6:
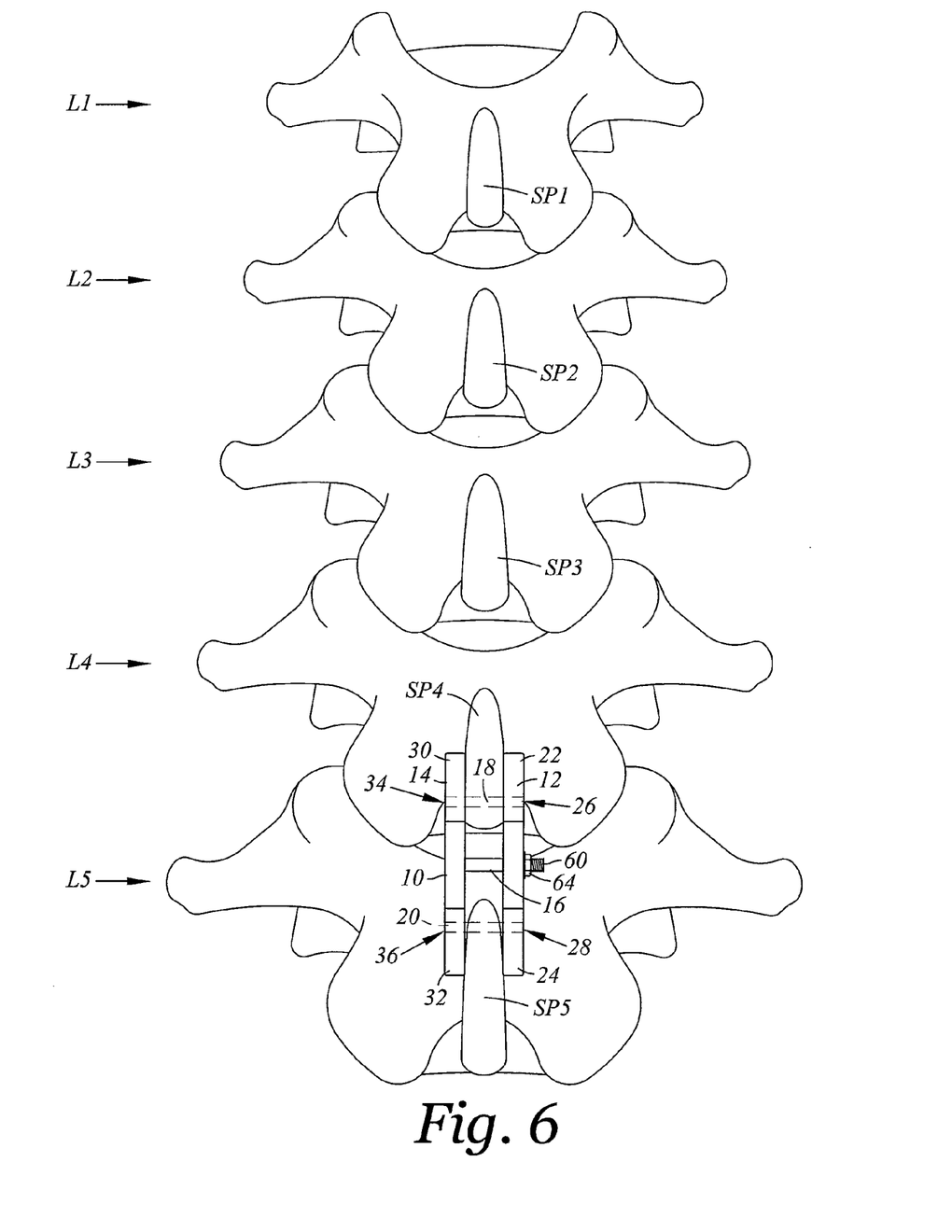
FIG. 6 is a posterior view illustrating the lumbar region of the spine taken along the sagittal plane with the spinal implant device installed.
Figures 7, 8:
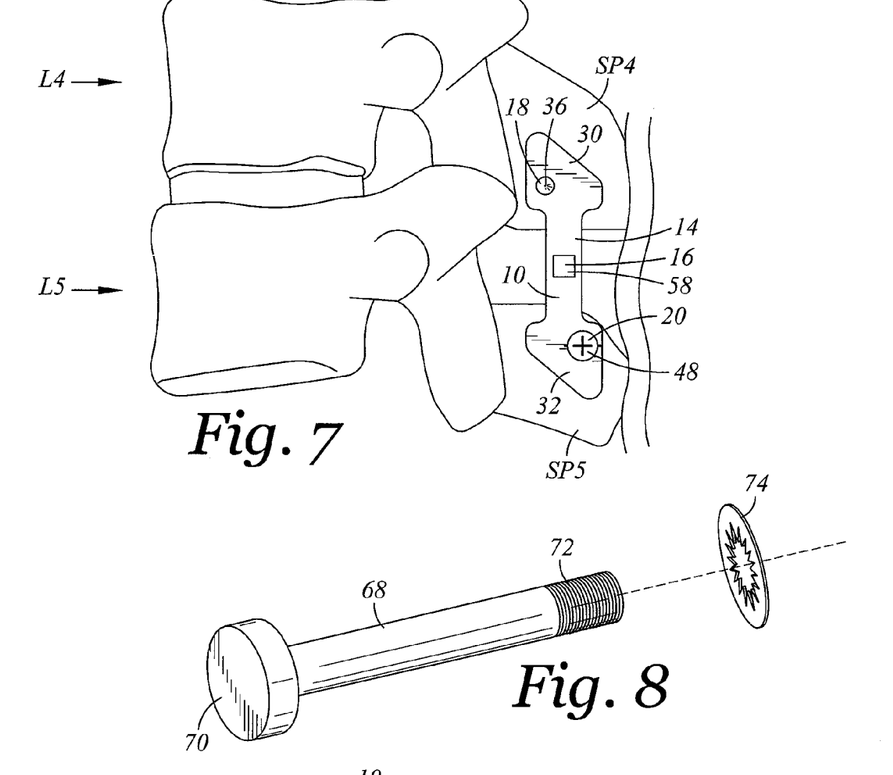
FIG. 7 is a side view illustrating the L4 and L5 vertebrae of FIG. 6 with the spinal implant device installed (with lag screws shown in phantom)
FIG. 8 is a connector of the a spinal implant device according to another embodiment.

The spinal implant device 10 is for use with installation within a spine. In this regard, referring additionally to FIG. 6, there is provided a posterior view illustrating the lumbar region of the spine taken along the sagittal plane with the spinal implant device 10 installed. The lumbar spine includes a series of stacked vertebrae (L1-5). Each vertebra (L4, L5) includes a spinous process (SP1-SP5). FIG. 7 is a side view illustrating the vertebrae (L4, L5) of FIG. 6 with the spinal implant device 10 installed (with lag screws 18, 20 shown in phantom). It is noted that while the figures depict the lumbar region of the spine, the spinal implant device 10 may be deployed at any portion of the spine.

In accordance with one embodiment, a spinal implant device 10 is provided for placement between adjacent spinous processes. For example, the spinal implant device 10 may be installed between the two vertebrae (such as L4 and L5). As used herein in the context of installation of the spinal implant device 10 between two vertebrae (such as L4 and L5), the term superior refers to that skeletal structure anatomically positioned relatively above and the terms inferior refers to that skeletal structure anatomically positioned below. In this regard, for example, the spinal implant device 10 may be installed between the vertebrae (L4, L5). The adjacent spinous processes would be the (SP4) and (SP5) with the spinous processes (SP4) being referred to the superior spinous process and the spinous process (SP5) being referred to the inferior spinous process. As such, in the example installation, the spinous processes include a superior spinous process (SP4) and an inferior spinous process (SP5).

In accordance with one embodiment, the spinal implant device 10 is provided for placement between adjacent spinous processes, such as (SP4) and (SP5). In this example installation, the spinous processes include the superior spinous process (SP4) and an inferior spinous process (SP5). The spinal implant device 10 includes first and second fixation plates 12, 14, a connector 16, and first and second lag screws 18, 20. The first fixation plate 12 includes a first superior end 22 and a first inferior end 24. The first superior end 22 includes a first screw hole 26. The first inferior end 24 includes a second screw hole 28. The first fixation plate 12 is sized and configured to extend between and along the spinous processes (SP4, SP5) with the first screw hole 26 adjacent the superior spinous process (SP4) and the second screw hole 28 adjacent the inferior spinous process (SP5). The second fixation plate 14 includes a second superior end 30 and a second inferior end 32. The second superior end 30 includes a third screw hole 34. The second inferior end 32 includes a fourth screw hole 36. The second fixation plate 14 is sized and configured to extend between and along the spinous processes (SP4) with the third screw hole 34 adjacent the superior spinous process (SP4) and the fourth screw hole 36 adjacent the inferior spinous process (SP5). The connector 16 is connected to the first fixation plate 12 between the first superior end 22 and the first inferior end 24 and to the second fixation plate 14 between the second superior end 30 and the second inferior end 32. The first lag screw 18 is sized and configured to extend through the first and third screw holes 26, 34 and threadedly engage a respective one of the first or third screw holes 26, 34 with the superior spinous process (SP4) disposed between the first and second superior ends 22, 30. In the embodiment depicted, the first lag screw 18 is threadedly engaged with the third screw hole 34. The second lag screw 20 is sized and configured to extend through the second and fourth screw holes 28, 36 and threadedly engage a respective one of the second or fourth screw holes 38, 36 with the inferior spinous process (SP5) disposed between the first and second inferior ends 24, 32. In the embodiment depicted, the second lag screw 20 is threadedly engaged with the second screw hole 28.

The present invention of fixation plate affixation utilizing lag screws is as novel in the sense that it has never been proposed before as it is transformative because of the fact that it overcomes the biomechanical deficiency of the present bone affixation methodology. The spinal implant device 10 with the first and second lag screws 18, 20 provides the subject motion segments with additional support in flexion, extension, and lateral rotation of the spine in comparison to the prior art fixation methodologies. In addition, because the first and second lag screws 18, 20 directly engage the first and second fixation plates 12, 14, there is no need for additional nuts or attachment components to attach the first and second lag screws 18, 20 to the first and second fixation plates 12, 14. This is contemplated to simplify the surgical procedure (i.e., not having to simultaneously engage a nut and screw in the screws) and mitigate the complication of any "dropped" nut or attachment components. The spinal implant device 10 may be implanted in through a minimally disruptive surgery. In this regard, muscle and ligaments attached to the transverse processes and facet joints need not be directly disturbed. The spinal implant device 10 may be deployed with a midline exposure minimally invasive retractor based system or in standard minimally open fashion. Moreover, the spinal implant device 10 can be utilized in a single or multi level construct and be extended up to three levels in any region of the spine. As such, it is contemplated that the use of the first and second lag screws 18, 20 significantly reduces the need for pedicle screw instrumentation and greatly increases the likelihood of fusion success in spine surgery.

In this embodiment, the first lag screw 18 includes a threaded end 38, a shank 40, and a head 42. The second lag screw 20 includes a threaded end 44, a shank 46, and a head 48. The first screw hole 26 is configured to receive the threaded end 38 and the shank 40 of the first lag screw 18 through the first screw hole 26. The first screw hole 26 includes a countersink portion 50 sized and configured to accommodate the screw head 42. The second screw hole 28 is threaded and cooperatively sized and configured to threadedly engage the threaded end 44 of the second lag screw 20. The third screw hole 34 is configured to receive the threaded end 38 and the shank 40 of the first lag screw 18 through the third screw hole 34. The fourth screw hole 36 is configured to receive the threaded end 44 and the shank 46 of the second lag screw 20 through the fourth screw hole 36. The forth screw hole 36 includes a countersink portion 52 sized and configured to accommodate the screw head 48. In this embodiment the heads 42, 48 each include an indenture of a Phillips head configuration. It is contemplated that the heads 42, 48 may be chosen from any of those which are well known to one of ordinary skill in the art and may be configured to be engaged with screwdrivers and other various tooling, such as wrenches.

During installation of the spinal implant device 10, the first lag screw 18 may be inserted through the first screw hole 26, through the spinous process (such as SP5), and into the third screw hole 34. Likewise, the second lag screw 20 may be inserted through the fourth screw hole 36, through the spinous process (such as SP4), and into the second screw hole 28. It is contemplated that by screwing the first and second lag screws 18, 20 respectively into the third and second screw holes 34, 28 the first and second fixation plates 12, 14 are drawn toward each other. The first and second fixation plates 12, 14 may thus be configured to apply a compressive force against the spinous processes (SP4, SP5) to lock the first and second fixation plates 12, 14 in place and to provide fixation of the associated motion segments.

As used herein the term "lag screw" refers to a fastener, such as a screw or bolt, with a threaded end that is configured to engage a corresponding threaded opening of an object to which it is being attached. In this regard, a lag screw does not require any additional nut that is separate and apart from the structure to which it is being attached. However, a nut may be integrated with the structure, such as a nut that is overmolded in a plastic material for example.

The first and second fixation plates 12, 14 are configured to receive the connector 16 there through. In this regard the second fixation plate 14 includes a connector opening 54 and the first fixation plate 12 includes a connector opening 56. The length of the connector 16 may facilitate an ease of attachment and positioning of the first and second fixation plates 12, 14 with regard to the superior and inferior spinous processes (SP4, SP5). The connector 16 is disposed in slidable engagement with the first and second fixation plates 12, 14. The connector 16 may include a connector head 58 and an opposing end 60. The connector head 58 may have a non-circular cross-section. In this embodiment the connector head 58 has a square cross-section. The connector head 58 is sized and configured to engage the connector opening 54 to prevent rotation of the connector head 58 when engaged with the connector opening 54. The shank of the connector 16 may also have a non-circular cross-section, such as a square cross-section as depicted. The connector 16 is configured to engage the connector opening 56. As such, in this embodiment, the first and second fixation plates 12, 14 are configured to pivot in unison with regard to a longitudinal axis along the connector 16. In this regard, the particular non-circular nature of the cross-sections of the connector head 58 and the shank of the connector 16 facilitate engagement with the first and second fixation plates 74, 76 to lock relative movement. Also in this embodiment, the end 60 of the connector 16 is sized and configured to receive a lock washer 62 and threadedly engage a nut 64. The connector 16 may be connected to the first and second fixation plates 12, 14 with the connector 16 sized and configured to compress the first and second fixation plates 12, 14 against the spinous processes (SP4, SP5). This allows for the spinal implant device 10 to be initially fixed in position with regard to the spinous processes (SP4, SP5), prior to the final installation using the first and second lag screws 18, 20.

Figure 12:
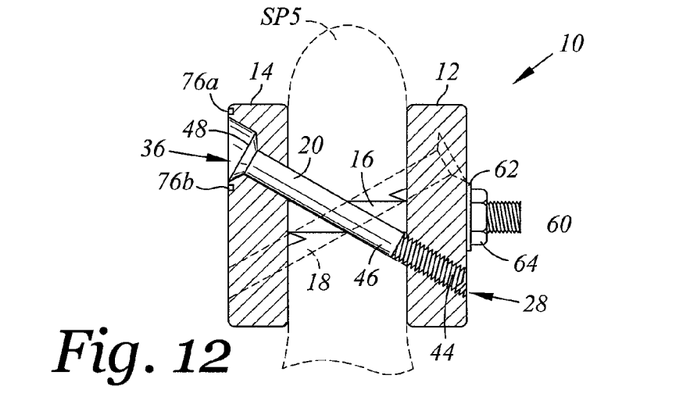
FIG. 12 is the end view of the spinal implant device and the spinous process (in phantom) of FIG. 11; however, with a first lag screw engaged with the spinal implant device and a second lag screw (in phantom) engaged with the spinal implant device.

Though not depicted, it is also contemplated that the connector 16 may be integrated with one of the first or second fixation plates 12, 14. For example in another embodiment, the connector 16 and the second fixation plate 14 are formed of a common material having material continuity. It is contemplated that the connector 16 may take various forms and modes of connection with regard to the first and second fixation plates 12, 14 according to any of those which are well known to one of ordinary skill in the art. It is contemplated that other arrangements for connecting the first and second fixation plates 12, 14, 16 may be implemented. As such any assortment of fasteners may be implemented, such as the configuration described below as seen in FIG. 12. Moreover, various degrees of freedom of the various connection points may be modified. For example, the connector 16 may be connected to the first and/second fixation plates 12, 14 with a ball joint.

Referring now to FIG. 12, there is depicted a perspective view of a connector 68 according to another embodiment. It is contemplated that the connector 68 may be used in place of the connector 16 described above. In this embodiment, the connector 68 takes the form of a pin and includes and end cap 70 and an opposing ribbed end 72. The connector 68 may be inserted through the connector opening 56 and then the connector opening 54. The end cap may be flush against the second fixation plate 14. The end cap 70 may be press fit onto the connector 68 or material of the connector 68 may be deformed so as to form the end cap 70. A lock washer 74 may be used to initially affix the first and second fixation plates 12, 14 into position. As one of ordinary skill in the art will appreciate, the selection of the connector 16 over the connector 68 (or any other embodiments) would depend upon the torque or compression strength requirements of the connector application. In addition, in this embodiment, the connector 68 has a circular cross-section and allows the first and second fixation plates 12, 14 to rotate with respect to each other about an axis along the connector 68.

The first and second fixation plates 12, 14 may each include teeth 66 for respectively engaging the spinous processes (SP4, SP5). The shape, number and sizing of the teeth 66 may vary depending upon such factors as material selection of the teeth 66 themselves and whether any other means of attaching the first and second fixation plates 12, 14 are utilized (such as the connector 16 to provide a compressive force of the first and second fixation plates 12, 14 to the spinous processes (SP4, SP5)). As mentioned above, the first and second fixation plates 12, 14 each are sized and configured to extend along the adjacent spinous processes (SP4, SP5) with the superior ends 22, 30 disposed about and in contact with the superior spinous process (SP4) and the inferior ends 24, 32 disposed about and in contact with the inferior spinous process (SP5). In this regard, the teeth 66 may be disposed at each of the superior ends 22, 30 and the inferior ends 24, 32 at such locations where the first and second fixation plates 12, 14 are intended to contact the spinous processes (SP4, SP5).

Suitable implant materials for the spinal implant device 10 may be chosen from those which are well known to one of ordinary skill in the art. In some embodiments, all components of the spinal implant device 10 may be of a same material or a combination of differing materials. It is contemplated that medical grade metals may be utilized, such as titanium, stainless steel, cobalt chrome, and alloys thereof. In this regard, other suitable materials include certain medical grade polymers. A group of biocompatible polymer is the polyaryl ester ketones which have several members including polyetheretherketone (PEEK) and polyetherketoneketone (PEKK). In an embodiment, the first and second fixation plates 12, 14 may be formed of titanium. The use of titanium may be particularly desirable for the fixation plates 12, 14 due to the strength characteristics with regard to the formation of the threads of the second and third screw holes 28, 34 and the teeth 66. In another embodiment, the fixation plates 12, 14, the connector 16, and even the first and second lag screws 18, 20 may all be formed of PEEK. This may be desirable as this would be a non-metal option.

The first and second fixation plates 12, 14 include the superior ends 22, 30 and the inferior ends 24, 32 that are tapered. Such tapering is contemplated to allow for similarly constructed spinal implant devices 10 to have their first and second fixation plates 12, 14 about each other where the spinal implant devices 10 are being deployed in a manner that shares a common spinous process (i.e., installations at adjacent levels).

In the embodiment depicted, the screw holes 26, 28, 34, 36 are disposed at an oblique angle through the first and second fixation plates 12, 14. In this regard, the first and second fixation plates 12, 14 may be generally planar and may each respectively define a superficial/deep plane. The screw holes 26, 28, 34, 36 may respectively extend through the first and second fixation plates 12, 14 at an angle less than 90 degrees, such as in a range of 60 to 30 degrees, with respect to the superficial/deep plane. Such an angle allows for an ease for the surgeon to insert the screws (as opposed to being inserted laterally which may require additional anatomical structures and matter to be disturbed).

Figures 10, 11:
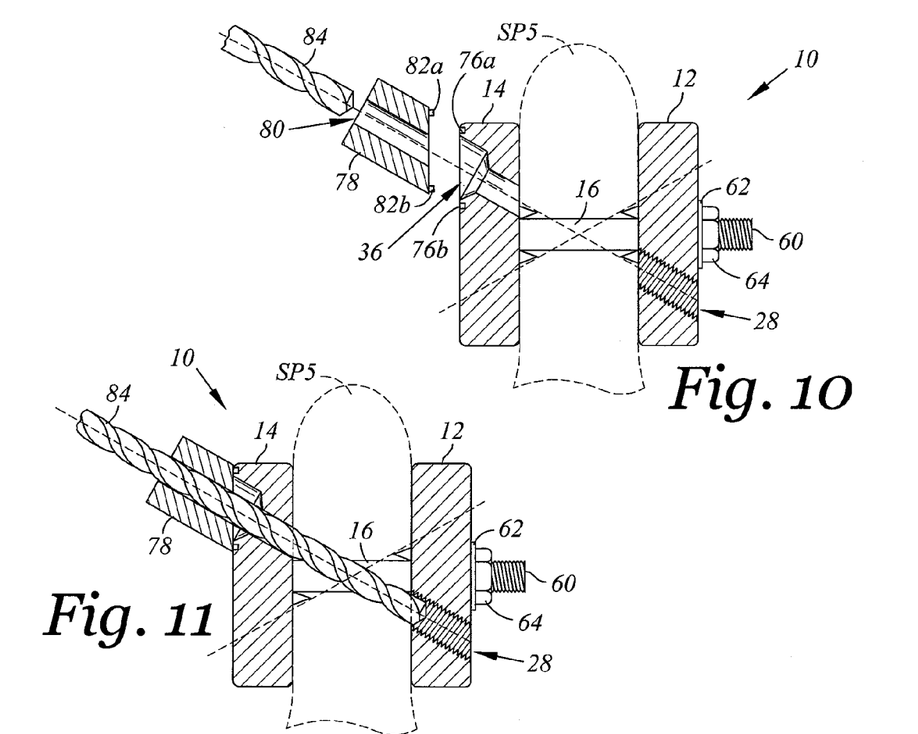
FIG. 10 is the end view of the spinal implant device and the spinous process (in phantom) of FIG. 9; however, with the lock washer and the nut attached and a drill guide and a portion of a drill bit.
FIG. 11 is the end view of the spinal implant device and the spinous process (in phantom) of FIG. 10; however, with the drill guide engaged with the spinal implant device and the drill bit inserted through the drill guide, the spinal implant device and the spinous process.

The second fixation plate 14 may include indexing features 76a, b that are disposed adjacent the fourth screw hole 36. As will be discussed below, such indexing features 76a, b may be used to engage a drill guide 78 (as depicted in FIGS. 10 and 11).

Figure 9:
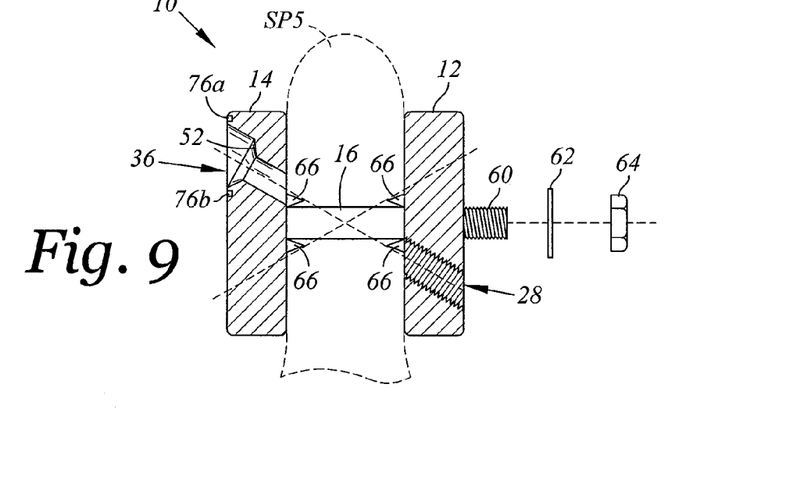
FIG. 9 is an end view similar to FIG. 5 of the spinal implant device, however, with a superior spinous process (in phantom), a lock washer and a nut (exploded) and without any lag screws.

According to another embodiment, there is provided a method of implanting the spinal implant device 10 for placement between adjacent spinous processes (such as between SP4 and SP5). The method initially includes providing the spinal implant device 10 including the first and second fixation plates 12, 14, such as described above. The method includes positioning the first fixation plate 12 along the spinous processes (SP4, SP5) with the first superior end 22 adjacent the superior spinous process (SP4) and the first inferior end 24 adjacent the inferior spinous process (SP5). Similarly, the method includes positioning the second fixation plate 14 along the spinous processes (SP4, SP5) with the second superior end 30 adjacent the superior spinous process (SP4) and the second inferior end 32 adjacent the inferior spinous process (SP5). Referring now to FIG. 9 there is an end view similar to the view of FIG. 5 of the spinal implant device 10 to FIG. 5, however, with a superior spinous process (in phantom) and a lock washer 62 and a nut 64 (exploded) and without the first and second lag screws 18, 20. In this view the first and second fixation plates 12, 14 are positioned adjacent the inferior spinous process (SP5). A posterior view of the first and second fixation plates 12, 14 as position along both of the spinous processes (SP4, SP5) is depicted in FIG. 6. The method further includes inserting the first lag screw 18 through the first and third screw holes 26, 34 and superior spinous process (SP4). The method further includes threadedly engaging the first lag screw 18 with a respective one of the first or third screw holes 26, 34. In the embodiment depicted, the first lag screw 18 is engaged with the third screw hole 34. The method further includes inserting the second lag screw 20 through the second and fourth screw holes 28, 36 and inferior spinous process (SP5). The method further includes threadedly engaging the second lag screw 20 with a respective one of the second or fourth screw holes 28, 36. In the embodiment depicted, the second lag screw 20 is engaged with the second screw hole 28. Referring additionally to FIG. 12 there is depicted the end view of the spinal implant device 10 similar to that of FIG. 9, however, with the first lag screw 18 engaged with the spinal implant device 10 and a second lag screw 20 (in phantom) engaged with the spinal implant device 10.

In further detail, according to various embodiments of the method of the present invention, an initial surgical window is created in preparation for the installation of the spinal implant device 10 by exposing the spinous processes (SP4, SP5). It is contemplated that the surgeon is provided with an array of spinal implant devices 10 having differing sized components. In particular, there may be provided various spinal implant devices 10 with varying sizes of the first and second fixation plates 12, 14. In addition, a variety of spinal implant devices 10 may each feature a differing installed spacing distance (D) between the first and second fixation plates 12, 14 and/or install lag screw angle (a) (as best seen in FIG. 5). The relative spacing between the first and second fixation plates 12, 14 is dictated to a large degree by the angle and placement in which the screw holes 26, 28, 34, 36 are formed respectively with regard to the first and second fixation plates 12, 14. As such, it is contemplated that the surgeon would have an array of similarly configured spinal implant devices 10 with differing spacing between the first and second fixation plates 12, 14 (with corresponding differing angulations and/or placement of the screw holes 26, 28, 34, 36). After the surgeon has created the necessary surgical window discussed above, a particular spinal implant device 10 may be chosen in reference to the width requirements associated with the spinous processes (SP4, SP5).

The method further includes attaching the first and second fixation plates 12, 14 to the adjacent spinous processes (SP4, SP5) with the spinous processes (SP4, SP5) disposed between the first and second fixation plates 12, 14. In this regard, the method may further include positioning the teeth 58 respectively against the spinous processes (SP4, SP5). In this regard, the method may include positioning the teeth 66 of the first and second fixation plates 12, 14 respectively against the spinous processes (SP4, SP5). The method may further include affixing the first and second fixation plates 12, 14 to the superior and inferior spinous processes (SP4, SP5) through the application of a compressive force. In this regard the end 60 of the connector 16 may be inserted through the second fixation plates 14 and through the first fixation plate 12. The lock washer 62 and the nut 64 may be engaged with the end 60 (as depicted in FIG. 10).

Prior to the insertion of the first and second lag screw 18, 20, the method would further include drilling a hole through each of the spinous processes (SP4, SP5). To facilitate such drilling, a drill guide 78 may be provided that is engaged with the first and second fixation plates 12, 14 respectively at the first and fourth screw holes 26, 36. The drill guide 78 is contemplated to aid in maintaining a drill bit 84 at a desired angle so as to align the drill bit 84 with the second and third screw holes 28, 34. Referring now to FIG. 10 is the end view of the spinal implant device 10 and the spinous process (in phantom) of FIG. 9, however, with the lock washer 62 and the nut 64 attached and the drill guide 78 and a portion of the drill bit 84.

The drill guide 78 may include a guide hole 80 that is used to laterally support the drill bit 84 with the drill bit 84 inserted through the guide hole 80. The drill guide 78 may further include alignment features 82a, b that are sized and configured to interlock with the indexing features 76a, b when the drill guide 78 is flush against the surface of the first and second fixation plates 12, 14. FIG. 11 is the end view of the spinal implant device 10 and the spinous process (in phantom) of FIG. 10, however, with the drill guide 78 engaged with the spinal implant device 10 and the drill bit 84 inserted through the drill guide 78, the spinal implant device 10 and the spinous process (SP5). In this regard, FIG. 11 depicts the drill guide 78 positioned against the second fixation plate 14 with the guide hole 80 aligned with the fourth screw hole 36.

The method may include inserting the drill bit 84 through the drill guide 78 through the fourth screw hole 36 of the second fixation plate 14, into and through the spinous process (SP5), and into the second screw hole 28. The second lag screw 20 may then be inserted through the fourth screw hole 36 of the second fixation plate 14, through the spinous process (SP5), and into the second screw hole 28 of the first fixation plate 18. The lag screw 20 is then screwed into the first fixation plate 12 with the threaded end 44 engaging the second screw hole 28. A like process would be performed with regard to the first lag screw 18, the first and third screw holes 26, 34, and the superior spinous process (SP4).

The particulars shown herein are by way of example only for purposes of illustrative discussion, and are presented in the cause of providing what is believed to be the most useful and readily understood description of the principles and conceptual aspects of the various embodiments set forth in the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A spinal implant device for use with adjacent spinous processes, the spinous processes including a superior spinous process and an inferior spinous process, the spinal implant device comprising:

a first fixation plate including a first superior end and a first inferior end, the first superior end including a first screw hole, the first inferior end including a second screw hole, the first fixation plate being sized and configured to extend between and along the spinous processes with the first screw hole adjacent the superior spinous process and the second screw hole adjacent the inferior spinous process;

a second fixation plate including a second superior end and a second inferior end, the second superior end including a threaded third screw hole having threads integral to the second fixation plate, the second inferior end including a fourth screw hole, the second fixation plate being sized and configured to extend between and along the spinous processes with the third screw hole adjacent the superior spinous process and the fourth screw hole adjacent the inferior spinous process, the first screw hole being coaxially aligned with the third screw hole along a first axis, the second screw hole being coaxially aligned with the fourth screw hole along a second axis angularly offset from the first axis;

a connector connected to the first fixation plate between the first superior end and the first inferior end and to the second fixation plate between the second superior end and the second inferior end;

a first lag screw sized and configured to extend through the first and third screw holes and threadedly engage a respective one of the first or third screw holes with the superior spinous process disposed between the first and second superior ends; and a second lag screw sized and configured to extend through the second and fourth screw holes and threadedly engage a respective one of the second or fourth screw holes with the inferior spinous process disposed between the first and second inferior ends.

2. The spinal implant device of claim 1 wherein the first lag screw is sized and configured to extend through the first screw hole and threadedly engage the third screw hole with the superior spinous process disposed between the first and second superior ends.

3. The spinal implant device of claim 2 wherein the second screw hole is threaded, the first fixation plate includes threads integral therewith, the second lag screw is sized and configured to extend through the fourth screw hole and threadedly engage the second screw hole with the inferior spinous process disposed between the first and second inferior ends.

4. The spinal implant device of claim 1 wherein the first fixation plate is generally planar and defining a superficial/deep plane, the first screw hole extends through the first fixation plate at an angle less than 90 degrees with respect to the superficial/deep plane.

5. The spinal implant device of claim 1 wherein the first fixation plate is generally planar and defining a superficial/deep plane, the first screw hole extends through the first fixation plate at an angle in the range of 60 to 30 degrees with respect to the superficial/deep plane.

6. The spinal implant device of claim 1 wherein the first and second fixation plates are each generally planar and each define a superficial/deep plane, the first and second fixation plates are configured to translate relative to each other along a lateral axis orthogonal to the superficial/deep planes.

7. The spinal implant device of claim 1 wherein the first and second fixation plates are angularly in fixed relation to each other.

8. The spinal implant device of claim 1 wherein the connector is a pin.

9. The spinal implant device of claim 1 wherein the connector is in slidable engagement with the second fixation plate.

10. The spinal implant device of claim 1 wherein the connector has a non-circular cross-section.

11. The spinal implant device of claim 1 wherein the connector is in fixed relation to the first fixation plate.

12. The spinal implant device of claim 1 wherein the first and second fixation plates each include teeth for respectively engaging the spinous processes.

13. The spinal implant device of claim 1 wherein the first screw hole extends through the first fixation plate along a first axis and the second screw hole extends through the first fixation plate along a second axis, the first and second axes being disposed in non-parallel relation to each other.

14. The spinal implant device of claim 1 wherein the first lag screw is threadedly engaged directly with the second fixation plate.

15. The spinal implant device of claim 14 wherein the second lag screw is threadedly engaged directly with the first fixation plate.

16. A spinal implant device for use with adjacent spinous processes, the spinous processes including a superior spinous process and an inferior spinous process, the spinal implant device comprising:
   a first fixation plate including a first superior end and a first inferior end, the first superior end including a first screw hole, the first inferior end including a second screw hole, the first fixation plate being sized and configured to extend between and along the spinous processes with the first screw hole adjacent the superior spinous process and the second screw hole adjacent the inferior spinous process, the first screw hole extending through the first fixation plate along a first axis, the second screw hole extending through the first fixation plate along a second axis, the first and second axes being disposed in non-parallel relation to each other;
   a second fixation plate including a second superior end and a second inferior end, the second superior end including a threaded third screw hole having threads integral to the second fixation plate, the second inferior end including a fourth screw hole, the second fixation plate being sized and configured to extend between and along the spinous processes with the third screw hole adjacent the superior spinous process and the fourth screw hole adjacent the inferior spinous process;
   a connector connected to the first fixation plate between the first superior end and the first inferior end and to the second fixation plate between the second superior end and the second inferior end;
   a first lag screw sized and configured to extend through the first and third screw holes and threadedly engage a respective one of the first or third screw holes with the superior spinous process disposed between the first and second superior ends; and
   a second lag screw sized and configured to extend through the second and fourth screw holes and threadedly engage a respective one of the second or fourth screw holes with the inferior spinous process disposed between the first and second inferior ends.

\* \* \* \* \*